(12) United States Patent
Behzadi

(10) Patent No.: US 10,470,897 B2
(45) Date of Patent: Nov. 12, 2019

(54) PROSTHESIS REVISION SYSTEMS AND METHODS

(71) Applicant: Kambiz Behzadi, Pleasanton, CA (US)

(72) Inventor: Kambiz Behzadi, Pleasanton, CA (US)

( * ) Notice: Subject to any disclaimer, the term of this patent is extended or adjusted under 35 U.S.C. 154(b) by 544 days.

(21) Appl. No.: 15/235,086

(22) Filed: Aug. 11, 2016

(65) Prior Publication Data

US 2017/0065428 A1    Mar. 9, 2017

Related U.S. Application Data

(63) Continuation-in-part of application No. 15/092,384, filed on Apr. 6, 2016, which is a continuation-in-part of application No. 14/923,203, filed on Oct. 26, 2015, now abandoned, which is a continuation-in-part of application No. 14/584,656, filed on Dec. 29, 2014, now Pat. No. 9,168,154.

(60) Provisional application No. 61/980,188, filed on Apr. 16, 2014, provisional application No. 61/921,528, filed on Dec. 29, 2013.

(51) Int. Cl.
*A61B 17/58* (2006.01)
*A61B 17/60* (2006.01)
*A61F 2/00* (2006.01)
*A61F 2/46* (2006.01)

(52) U.S. Cl.
CPC .... *A61F 2/4609* (2013.01); *A61F 2002/4619* (2013.01); *A61F 2002/4623* (2013.01); *A61F 2002/4666* (2013.01); *A61F 2002/4681* (2013.01); *A61F 2002/4694* (2013.01)

(58) Field of Classification Search
CPC combination set(s) only.
See application file for complete search history.

(56) References Cited

U.S. PATENT DOCUMENTS

| | | |
|---|---|---|
| 5,007,936 A | 4/1991 | Woolson |
| 5,019,083 A | 5/1991 | Klapper et al. |
| 5,061,270 A | 10/1991 | Aboczky |
| 5,112,338 A | 5/1992 | Anspach, III |

(Continued)

FOREIGN PATENT DOCUMENTS

| | | |
|---|---|---|
| CA | 2934278 | 7/2015 |
| CA | 2934278 A1 | 7/2015 |

(Continued)

OTHER PUBLICATIONS

U.S. Appl. No. 16/278,093, filed Feb. 16, 2019, Kambiz Behzadi.

(Continued)

*Primary Examiner* — Sameh R Boles
(74) *Attorney, Agent, or Firm* — Patent Law Offices of Michael E. Woods; Michael E. Woods

(57) ABSTRACT

A system and method for allowing any surgeon, including those surgeons who perform a fewer number of a revision procedure as compared to a more experienced surgeon who performs a greater number of procedures, to provide an improved likelihood of a favorable outcome approaching, if not exceeding, a likelihood of a favorable outcome as performed by a very experienced surgeon with the revision procedure. An engine is operable in two distinctive selectable modes including a unidirectional mode providing only extractive forces and a bidirectional mode providing both extractive and insertional forces.

8 Claims, 10 Drawing Sheets

(56) References Cited

U.S. PATENT DOCUMENTS

| | | | |
|---|---|---|---|
| 5,169,399 | A | 12/1992 | Ryland et al. |
| 5,236,433 | A | 8/1993 | Salyer |
| 5,318,570 | A | 6/1994 | Hood et al. |
| 5,456,686 | A | 10/1995 | Klapper et al. |
| 5,540,697 | A | 7/1996 | Rehmann et al. |
| 5,571,111 | A | 11/1996 | Aboczky |
| 5,683,395 | A | 11/1997 | Mikhail |
| 6,228,092 | B1 | 5/2001 | Mikhail |
| 6,723,102 | B2 | 4/2004 | Johnson et al. |
| 6,884,264 | B2 | 4/2005 | Spiegelberg et al. |
| 6,917,827 | B2 | 7/2005 | Kienzle, III |
| 7,220,264 | B1 | 5/2007 | Hershberger |
| 7,326,217 | B2 | 2/2008 | Bubb |
| 7,559,931 | B2 | 7/2009 | Stone |
| 7,604,637 | B2 | 10/2009 | Johnson et al. |
| 7,645,281 | B2 | 1/2010 | Marik |
| 7,727,282 | B2 | 6/2010 | Slone et al. |
| 3,057,479 | A1 | 11/2011 | Stone |
| 8,057,482 | B2 | 11/2011 | Stone et al. |
| 8,118,815 | B2 | 2/2012 | van der Walt |
| 8,128,631 | B2 | 3/2012 | Johnson et al. |
| 8,167,823 | B2 | 5/2012 | Nycz et al. |
| 8,206,405 | B2 | 6/2012 | Beverland et al. |
| 8,216,286 | B2 | 7/2012 | Aeschlimann et al. |
| 8,496,657 | B2 | 7/2013 | Bonutti et al. |
| 8,556,909 | B2 | 10/2013 | Giersch et al. |
| 8,801,724 | B2 | 8/2014 | Zumsteg et al. |
| 8,888,786 | B2 | 11/2014 | Stone et al. |
| 8,911,447 | B2 | 12/2014 | van der Walt et al. |
| 8,974,467 | B2 | 3/2015 | Stone |
| 8,974,468 | B2 | 3/2015 | Borja |
| 8,998,910 | B2 | 4/2015 | Borja et al. |
| 9,168,154 | B2 | 10/2015 | Behzadi |
| 9,192,392 | B2 | 11/2015 | van der Walt et al. |
| 9,220,612 | B2 | 12/2015 | Behzadi |
| 9,271,756 | B2 | 3/2016 | van der Walt et al. |
| 9,649,202 | B2 | 5/2017 | Behzadi et al. |
| 2002/0193797 | A1 | 12/2002 | Johnson et al. |
| 2005/0119666 | A1 | 6/2005 | Bubb |
| 2006/0100548 | A1 | 5/2006 | Ferguson |
| 2008/0109008 | A1 | 5/2008 | Schwager et al. |
| 2008/0119845 | A1 | 5/2008 | Stone et al. |
| 2009/0318836 | A1 | 12/2009 | Stone et al. |
| 2009/0318930 | A1 | 12/2009 | Stone et al. |
| 2009/0318931 | A1 | 12/2009 | Stone et al. |
| 2010/0016705 | A1 | 1/2010 | Stone |
| 2010/0063508 | A1 | 3/2010 | Borja et al. |
| 2010/0063509 | A1 | 3/2010 | Borja et al. |
| 2010/0064216 | A1 | 3/2010 | Borja et al. |
| 2010/0069911 | A1 | 3/2010 | Borja et al. |
| 2010/0076505 | A1 | 3/2010 | Borja |
| 2010/0100139 | A1 | 4/2010 | Young |
| 2010/0137869 | A1 | 6/2010 | Borja et al. |
| 2010/0137871 | A1 | 6/2010 | Borja |
| 2010/0249796 | A1 | 9/2010 | Nycz |
| 2011/0208093 | A1 | 8/2011 | Gross et al. |
| 2011/0218543 | A1 | 9/2011 | van der Walt |
| 2011/0251600 | A1 | 10/2011 | Giersch et al. |
| 2012/0130279 | A1 | 5/2012 | Stone |
| 2012/0136361 | A1 | 5/2012 | Aux Epaules et al. |
| 2012/0209277 | A1 | 8/2012 | Leparmentier et al. |
| 2012/0283599 | A1 | 11/2012 | Borja |
| 2012/0316567 | A1 | 12/2012 | Gross et al. |
| 2013/0066323 | A1 | 3/2013 | Nycz et al. |
| 2013/0149660 | A1 | 6/2013 | Pruckner et al. |
| 2013/0282014 | A1 | 10/2013 | Haimerl et al. |
| 2014/0012391 | A1 | 1/2014 | Gugler et al. |
| 2014/0052149 | A1 | 2/2014 | van der Walt et al. |
| 2014/0058526 | A1 | 2/2014 | Meridew et al. |
| 2014/0135791 | A1 | 5/2014 | Nikou et al. |
| 2014/0248581 | A1* | 9/2014 | Petersen ............. A61C 8/0089 433/119 |
| 2015/0182350 | A1 | 7/2015 | Behzadi |
| 2015/0182351 | A1 | 7/2015 | Behzadi |
| 2015/0320428 | A1 | 11/2015 | Roger |
| 2016/0095720 | A1 | 4/2016 | Behzadi |
| 2016/0100958 | A1 | 4/2016 | Behzadi et al. |
| 2016/0175110 | A1 | 6/2016 | Behzadi et al. |
| 2016/0199199 | A1 | 7/2016 | Pedicini |
| 2016/0213493 | A1 | 7/2016 | Behzadi |
| 2017/0065428 | A1 | 3/2017 | Behzadi |
| 2017/0065429 | A1 | 3/2017 | Behzadi et al. |
| 2017/0071759 | A1 | 3/2017 | Behzadi et al. |
| 2017/0196705 | A1 | 7/2017 | Behzadi |
| 2017/0202683 | A1 | 7/2017 | Behzadi |
| 2017/0290666 | A1 | 10/2017 | Behzadi |

FOREIGN PATENT DOCUMENTS

| | | |
|---|---|---|
| EP | 3089685 | 11/2016 |
| EP | 3089685 A1 | 11/2016 |
| FR | 2741523 | 5/1997 |
| FR | 2741523 A1 | 5/1997 |
| JP | 2017500984 | 1/2017 |
| JP | 2017500984 A | 1/2017 |
| WO | 8802246 | 4/1988 |
| WO | 8802246 A2 | 4/1988 |
| WO | 9740785 | 11/1997 |
| WO | 0108569 | 2/2001 |
| WO | 0108569 A1 | 2/2001 |
| WO | 2008003962 | 1/2008 |
| WO | 2008003962 A1 | 1/2008 |
| WO | 2015100461 | 7/2015 |
| WO | 2015100461 A1 | 7/2015 |
| WO | 2017176905 | 10/2017 |
| WO | 2017176905 A1 | 10/2017 |

OTHER PUBLICATIONS

U.S. Appl. No. 16/280,044, filed Feb. 20, 2019, Kambiz Behzadi.
U.S. Appl. No. 61/921,528, filed Dec. 29, 2013, Kambiz Behzadi.
U.S. Appl. No. 61/980,188, filed Apr. 16, 2014, Kambiz Behzadi.
U.S. Appl. No. 14/584,656, filed Dec. 29, 2014, Kambiz Behzadi.
U.S. Appl. No. 14/585,056, filed Dec. 29, 2014, Kambiz Behzadi.
U.S. Appl. No. 14/923,203, filed Oct. 26, 2015, Kambiz Behzadi.
U.S. Appl. No. 14/965,851, filed Dec. 10, 2015, Kambiz Behzadi.
U.S. Appl. No. 14/969,721, filed Dec. 15, 2015, Kambiz Behzadi et al.
U.S. Appl. No. 15/055,942, filed Feb. 29, 2016, Kambiz Behzadi et al.
U.S. Appl. No. 15/092,384, filed Apr. 6, 2016, Kambiz Behzadi.
U.S. Appl. No. 15/235,078, filed Aug. 11, 2016, Kambiz Behzadi et al.
U.S. Appl. No. 15/235,094, filed Aug. 11, 2016, Kambiz Behzadi et al.
U.S. Appl. No. 15/479,716, filed Apr. 5, 2017, Kambiz Behzadi.
U.S. Appl. No. 16/050,662, filed Jul. 31, 2018, Kambiz Behzadi et al.
The WoodPecker, Total Hip Broaching System, General Information, 1992, [retrieved on Feb. 13, 2015], Retrieved from the Internet: <www.imt-medicalusa.com/products/woodpecker-hip-broaching-system.aspx>.
The WoodPecker, Total Hip Broaching System, Specification, 1992, [retrieved on Feb. 13, 2015], Retrieved from the Internet: <www.imt-medicalusa.com/products/woodpecker-specifications.aspx>.
The WoodPecker, Total Hip Broaching System, Operation Manual, 1992, [retrieved on Feb. 13, 2015], Retrieved from the Internet: <www.plusmed.si/uploads/datoteke/Pnevmatsko%20kladivo%20-%20navodilo%20za%20uporabo.pdf>.
The WoodPecker, Total Hip Broaching System, YourTube Reference—Total Hip Replacement with the Woodpecker Pneumatic Broaching System (2002), Uploaded Nov. 4, 2009, [retrieved on Feb. 13, 2015], Retrieved from the Internet: <www.youtube.com/watch?v=KisN6_M-xS0>.
Written Opinion of the International Searching Authority regarding International Application No. PCT/US2014/072609, dated Apr. 7, 2015.
International Search Report regarding International Application No. PCT/US2014/072609, dated Apr. 7, 2015.

(56) References Cited

OTHER PUBLICATIONS

International Search Report for International Application No. PCT/US17/19940 dated Jul. 13, 2017.
Written Opinion of the International Searching authority for International application No. PCT/US17/19940 dated Jul. 13, 2017.
U.S. Appl. No. 14/585,056, filed Dec. 29, 2014, Kambiz Behzadi et al.
International Search Report for International application No. PCT/US2017/026180 dated Sep. 8, 2017.
Written opinion of the international searching authority regarding International application No. PCT/US2017/026180 dated Sep. 8, 2017.

* cited by examiner

PROSTHESIS REVISION SYSTEMS AND METHODS

CROSS REFERENCE TO RELATED APPLICATIONS

This application is a continuation-in-part of U.S. patent application Ser. No. 15/092,384 filed 6 Apr. 2016 which is a continuation-in-part of U.S. patent application Ser. No. 14/923,203 filed 26 Mar. 2015 which is a continuation-in-part of U.S. patent application Ser. No. 14/584,656, filed 29 Dec. 2014 that in turn claims benefit of both U.S. Patent Application No. 61/921,528 and U.S. Patent Application No. 61/980,188, the contents of these applications in their entireties are hereby expressly incorporated by reference thereto for all purposes.

FIELD OF THE INVENTION

The present invention relates generally to orthopedic surgical systems and procedures employing a prosthetic implant for, and more specifically, but not exclusively, to joint replacement therapies such as total hip replacement including controlled installation, positioning, and revisioning of the prosthesis such as during removal and replacement of a prosthetic implant.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Total hip replacement refers to a surgical procedure where a hip joint is replaced using a prosthetic implant. There are several different techniques that may be used, but all include a step of inserting an acetabular component into the acetabulum and positioning it correctly in three dimensions (along an X, Y, and Z axis).

In total hip replacement (THR) procedures there are advantages to patient outcome when the procedure is performed by a surgeon specializing in these procedures. Patients of surgeons who do not perform as many procedures can have increased risks of complications, particularly of complications arising from incorrect placement and positioning of the acetabular component.

The incorrect placement and positioning may arise even when the surgeon understood and intended the acetabular component to be inserted and positioned correctly. This is true because in some techniques, the tools for actually installing the acetabular component are crude and provide an imprecise, unpredictable coarse positioning outcome.

It is known in some techniques to employ automated and/or computer-assisted navigation tools, for example, x-ray fluoroscopy or computer guidance systems. There are computer assisted surgery techniques that can help the surgeon in determining the correct orientation and placement of the acetabular component. However, current technology provides that at some point the surgeon is required to employ a hammer/mallet to physically strike a pin or alignment rod. The amount of force applied and the location of the application of the force are variables that have not been controlled by these navigation tools. Thus even when the acetabular component is properly positioned and oriented, when actually impacting the acetabular component into place the actual location and orientation can differ from the intended optimum location and orientation. In some cases the tools used can be used to determine that there is, in fact, some difference in the location and/or orientation. However, once again the surgeon must employ an impacting tool (e.g., the hammer/mallet) to strike the pin or alignment rod to attempt an adjustment. However the resulting location and orientation of the acetabular component after the adjustment may not be, in fact, the desired location and/or orientation. The more familiar that the surgeon is with the use and application of these adjustment tools can reduce the risk to a patient from a less preferred location or orientation. In some circumstances, quite large impacting forces are applied to the prosthesis by the mallet striking the rod; these forces make fine tuning difficult at best and there is risk of fracturing and/or shattering the acetabulum during these impacting steps.

Surgical procedures relating to prostheses includes various revision procedures in addition to an initial installation or assembly. These revision procedures include removal of a prosthesis (or disassembly of an assembled modular prosthesis) which can be improved. One of the primary steps in hip, knee and shoulder revision surgery is the extraction of the retained components before surgical reconstruction. In revision surgery, the removal of components that are well fixed to bone and or cement can be a very difficult, demanding, and time consuming. Typically, significant damage is done to the remaining host bone by application of large impact forces with 3 lb to 4 lb mallets or slap-hammers. In general the retained prosthesis is grasped in some fashion (i.e. either through a hook and hole, vise grip, or threaded screw) this part of the tool is then attached to a C-clamp with an impaction plate or a slide-hammer (slap-hammer) for application of the impact force (in reverse to installation impact) for extraction of the prosthesis.

What is needed is a system and method for allowing any surgeon, including those surgeons who perform a fewer number of a revision procedure as compared to a more experienced surgeon who performs a greater number of procedures, to provide an improved likelihood of a favorable outcome approaching, if not exceeding, a likelihood of a favorable outcome as performed by a very experienced surgeon with the revision procedure.

BRIEF SUMMARY OF THE INVENTION

Disclosed is a system and method for allowing any surgeon, including those surgeons who perform a fewer number of a revision procedure as compared to a more experienced surgeon who performs a greater number of procedures, to provide an improved likelihood of a favorable outcome approaching, if not exceeding, a likelihood of a favorable outcome as performed by a very experienced surgeon with the revision procedure.

The following summary of the invention is provided to facilitate an understanding of some of technical features related to total hip replacement, and is not intended to be a full description of the present invention. A full appreciation of the various aspects of the invention can be gained by taking the entire specification, claims, drawings, and abstract as a whole. The present invention is applicable to other surgical procedures, including replacement of other joints replaced by a prosthetic implant in addition to replacement of an acetabulum (hip socket) with an acetabular component (e.g., a cup). Use of pneumatic and electric motor implementations have both achieved a proof of concept development.

The disclosed concepts involve creation of a system/method/tool/gun that vibrates an attached prosthesis, e.g., an acetabular cup, and/or applies controllable extraction forces to an installed/assembled prosthesis. The gun would be held in a surgeon's hands and deployed. It would use a vibratory energy to insert (not impact) and position the cup into desired alignment (using current intra-operation measurement systems, navigation, fluoroscopy, and the like) or to extract (again without impact) and remove an installed prosthesis or aid in disassembly of an assembled modular prosthesis.

An embodiment of the present invention may include an application of extraction forces (required for removal of prosthesis) in orthopedic revision surgery. Use of a tool, such as a BMD vibrational tool, allows superior control of extraction force as compared to the use of the large 3 to 4 lb. mallets applying impact forces for removing a bonded prosthesis. The application of impact force with the 4 lb. mallet is often required for removal a well fixed prosthesis, however, at great cost and damage to the host bone. This makes the subsequent attempt at reconstruction more difficult and the chance of better outcome for the patient is reduced. The components of the extraction force (e.g., frequency and magnitude) can be modulated to just the right amount that is required to remove the prosthesis, avoiding excessive forces which can damage the severely compromised bone encountered in revision surgery. Some embodiments may give the surgeon a nuance and control henceforth not available. In this manner the surgeon is avoided more finesse and ability to remove the prosthesis quickly and safely.

One problem with conventional revision procedures include use of large and uncontrolled impact forces in orthopedic surgery and particularly in joint replacement. The incorporated patent and references have addressed a use of insertion (non-impact) forces for insertion of prosthesis and implants, which suggests that ultimately the use of force in orthopedics will be standardized and modulated and reduce or eliminate uncontrolled impact forces. Embodiments of the present invention may include adaptations and reconfigurations of the installation tools and concepts for use of applying controllable extraction forces in orthopedics. An ability to modulate and control extractive forces in orthopedics (required for removal of implants and rods, for example) gives the surgeon a better and safer way to remove implants and perform revision (arthroplasty) surgery.

In one embodiment, a first gun-like device is used for accurate impaction of the acetabular component at the desired location and orientation.

In another embodiment, a second gun-like device is used for fine-tuning of the orientation of the acetabular component, such as one installed by the first gun-like device, by traditional mallet and tamp, or by other methodology. However the second gun-like device may be used independently of the first gun-like device for adjusting an acetabular component installed using an alternate technique. Similarly the second gun-like device may be used independently of the first gun-like device, particularly when the initial installation is sufficiently close to the desired location and orientation. These embodiments are not necessarily limited to fine-tuning as certain embodiments permit complete re-orientation. Some implementations allow for removal of an installed prosthesis.

Another embodiment includes a third gun-like device that combines the functions of the first gun-like device and the second gun-like device. This embodiment enables the surgeon to accurately locate, insert, orient, and otherwise position the acetabular component with the single tool.

Another embodiment includes a fourth device that installs the acetabular component without use of the mallet and the rod, or use of alternatives to strike the acetabular component for impacting it into the acetabulum. This embodiment imparts a vibratory motion to an installation rod coupled to the acetabular component that enables low-force, impactless installation and/or positioning.

An embodiment of the present invention includes use, adaptation, and/or reconfiguration of installation tools described herein for use in extracting (without impact) an installed prosthesis.

An embodiment of the present invention includes use, adaptation, and/or reconfiguration of installation tools described herein for use in disassembling (without impact) an assembled modular prosthesis.

A positioning device for an acetabular cup disposed in a bone, the acetabular cup including an outer shell having a sidewall defining an inner cavity and an opening with the sidewall having a periphery around the opening and with the acetabular cup having a desired abduction angle relative to the bone and a desired anteversion angle relative to the bone, including a controller including a trigger and a selector; a support having a proximal end and a distal end opposite of the proximal end, the support further having a longitudinal axis extending from the proximal end to the distal end with the proximal end coupled to the controller, the support further having an adapter coupled to the distal end with the adapter configured to secure the acetabular cup; and a number N, the number N, an integer greater than or equal to 2, of longitudinal actuators coupled to the controller and disposed around the support generally parallel to the longitudinal axis, each the actuator including an associated impact head arranged to strike a portion of the periphery, each impact head providing an impact strike to a different portion of the periphery when the associated actuator is selected and triggered; wherein each the impact strike adjusts one of the angles relative to the bone.

An installation device for an acetabular cup disposed in a pelvic bone, the acetabular cup including an outer shell having a sidewall defining an inner cavity and an opening with the sidewall having a periphery around the opening and with the acetabular cup having a desired installation depth relative to the bone, a desired abduction angle relative to the bone, and a desired anteversion angle relative to the bone, including a controller including a trigger; a support having a proximal end and a distal end opposite of said proximal end, said support further having a longitudinal axis extending from said proximal end to said distal end with said proximal end coupled to said controller, said support further having an adapter coupled to said distal end with said adapter configured to secure the acetabular cup; and an oscillator coupled to said controller and to said support, said oscillator configured to control an oscillation frequency and an oscillation magnitude of said support with said oscillation frequency and said oscillation magnitude configured to install the acetabular cup at the installation depth with the desired abduction angle and the desired anteversion angle without use of an impact force applied to the acetabular cup.

An installation system for a prosthesis configured to be implanted into a portion of bone at a desired implantation depth, the prosthesis including an attachment system, including an oscillation engine including a controller coupled to a vibratory machine generating an original series of pulses having a generation pattern, said generation pattern defining a first duty cycle of said original series of pulses; and a pulse transfer assembly having a proximal end coupled to said oscillation engine and a distal end, spaced from said proximal end, coupled to the prosthesis with said pulse transfer assembly including a connector system at said proximal end, said connector system complementary to the attachment system and configured to secure and rigidly hold the prosthesis producing a secured prosthesis with said pulse transfer assembly communicating an installation series of pulses, responsive to said original series of pulses, to said secured prosthesis producing an applied series of pulses responsive to said installation series of pulses; wherein said applied series of pulses are configured to impart a vibratory motion to said secured prosthesis enabling an installation of said secured prosthesis into the portion of bone to within 95% of the desired implantation depth without a manual impact.

A method for installing an acetabular cup into a prepared socket in a pelvic bone, the acetabular cup including an outer shell having a sidewall defining an inner cavity and an opening with the sidewall having a periphery around the opening and with the acetabular cup having a desired installation depth relative to the bone, a desired abduction angle relative to the bone, and a desired anteversion angle relative to the bone, including (a) generating an original series of pulses from an oscillation engine; (b) communicating said original series of pulses to the acetabular cup producing a communicated series of pulses at said acetabular cup; (c) vibrating, responsive to said communicated series of pulses, the acetabular cup to produce a vibrating acetabular cup having a predetermined vibration pattern; and (d) inserting the vibrating acetabular cup into the prepared socket within a first predefined threshold of the installation depth with the desired abduction angle and the desired anteversion angle without use of an impact force applied to the acetabular cup.

This method may further include (e) orienting the vibrating acetabular cup within the prepared socket within a second predetermined threshold of the desired abduction angle and within third predetermined threshold of the desired anteversion angle.

A method for inserting a prosthesis into a prepared location in a bone of a patient at a desired insertion depth wherein non-vibratory insertion forces for inserting the prosthesis to the desired insertion depth are in a first range, the method including (a) vibrating the prosthesis using a tool to produce a vibrating prosthesis having a predetermined vibration pattern; and (b) inserting the vibrating prosthesis into the prepared location to within a first predetermined threshold of the desired insertion depth using vibratory insertion forces in a second range, said second range including a set of values less than a lowest value of the first range.

An extraction device for a prosthesis disposed in a bone having an exposed portion, including a controller including a trigger; a support having a proximal end and a distal end opposite of the proximal end, the support further having a longitudinal axis extending from the proximal end to the distal end with the proximal end coupled to the controller, the support further having an adapter coupled to the distal end with the adapter configured to engage the exposed portion of the prosthesis; and an oscillator coupled to the controller and to the support, the oscillator configured to control a series of vibratory pulses having an oscillation frequency and an oscillation magnitude of the support with the oscillation frequency and the oscillation magnitude configured to extract the prosthesis responsive to the series of vibratory pulses without impact forces.

An extraction system for a prosthesis installed and bonded into a portion of bone, the prosthesis including an exposed portion, comprising: an oscillation engine including a controller coupled to a vibratory machine generating an original series of pulses having a generation pattern, the generation pattern defining a first duty cycle of the original series of pulses; and a pulse transfer assembly having a proximal end coupled to the oscillation engine and a distal end, spaced from the proximal end, coupled to the prosthesis with the pulse transfer assembly including a connector system at the proximal end, the connector system configured to secure the exposed portion of the prosthesis producing a secured prosthesis with the pulse transfer assembly communicating an extraction series of pulses, responsive to the original series of pulses, to the secured prosthesis producing an applied series of ultrasonic pulses responsive to the extraction series of pulses; wherein the applied series of ultrasonic pulses are configured to impart a vibratory motion to the secured prosthesis enabling an extraction of the secured prosthesis from the portion of bone.

A method for extracting a prosthesis bonded within a portion of bone, the prosthesis having an exposed portion, including: (a) engaging the exposed portion; (b) generating an original series of pulses from an oscillation engine; (c) communicating the original series of pulses to the prosthesis producing a communicated series of pulses at the prosthesis; (d) vibrating, responsive to the communicated series of pulses, the prosthesis to produce a vibrating prosthesis having a predetermined vibration pattern; and (e) extracting the vibrating prosthesis from the portion of bone.

A method for extracting an implant bonded within a live bone of a patient, the prosthesis having an exposed portion, wherein non-vibratory revision forces for removing the bonded implant from the living bone are in a first range, the method including: (a) engaging the exposed portion; (b) vibrating the implant using a tool to produce a vibrating implant having a predetermined vibration pattern including an oscillation; and (c) extracting the vibrating implant from the live bone using vibratory insertion forces in a second range, the second range including a set of values less than a lowest value of the first range.

An apparatus for extracting a bonded implant from a live bone of a patient, the prosthesis having an exposed portion, wherein non-vibratory revision forces for removing the bonded prosthesis from the live bone are in a first range, including: means for vibrating the bonded implant to produce a vibrating bonded implant having a predetermined vibration pattern including an oscillation; and means for extracting the vibrating bonded implant from the live bone using vibratory extraction forces in a second range, the second range including a set of values less than a lowest value of the first range.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

Figure 1:
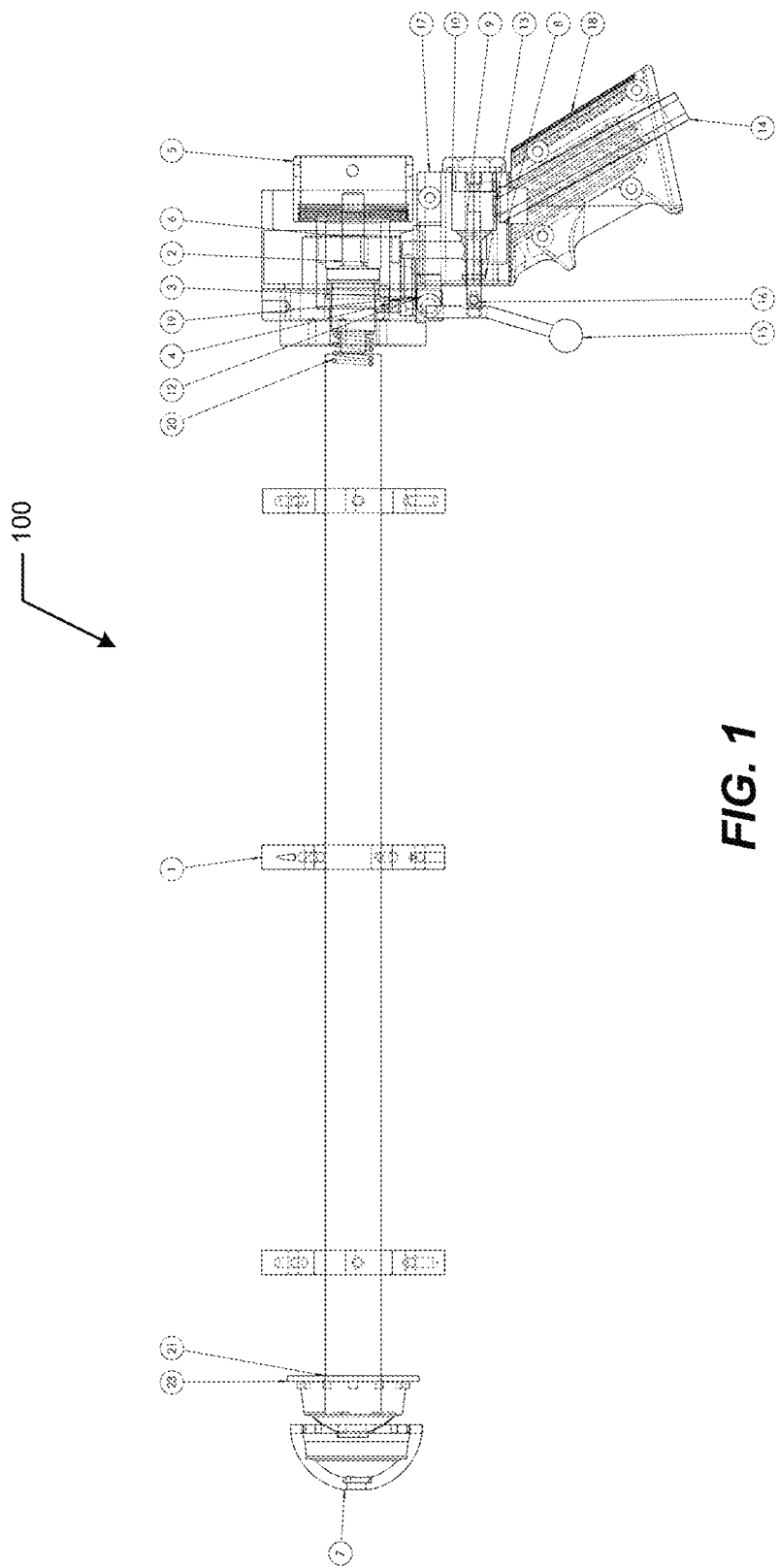
FIG. 1 illustrates a representative installation gun.

Embodiments of the present invention provide a system and method for allowing any surgeon, including those surgeons who perform a fewer number of a revision procedure as compared to a more experienced surgeon who performs a greater number of procedures, to provide an improved likelihood of a favorable outcome approaching, if not exceeding, a likelihood of a favorable outcome as performed by a very experienced surgeon with the revision procedure. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "bone" means rigid connective tissue that constitute part of a vertebral skeleton, including mineralized osseous tissue, particularly in the context of a living patient undergoing a prosthesis implant into a portion of cortical bone. A living patient, and a surgeon for the patient, both have significant interests in reducing attendant risks of conventional implanting techniques including fracturing/shattering the bone and improper installation and positioning of the prosthesis within the framework of the patient's skeletal system and operation.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

As used herein, mallet or hammer refers to an orthopedic device made of stainless steel or other dense material having a weight generally a carpenter's hammer and a stonemason's lump hammer.

As used herein, an impact force for impacting an acetabular component (e.g., an acetabular cup prosthesis) includes forces from striking an impact rod multiple times with the orthopedic device that are generally similar to the forces that may be used to drive a three inch nail into a piece of lumber using the carpenter's hammer by striking the nail approximately a half-dozen times to completely seat the nail. Without limiting the preceding definition, a representative value in some instances includes a force of approximately 10 lbs/square inch.

As used herein, the term "vibration" or "vibratory" refers to a mechanical displacement oscillations (repetitive positional variation in time) about an equilibrium point that includes one or more axes of motion. The equilibrium point may, in turn, move, such as for impactless implantation in which the equilibrium point is deeper into an installation site, for example, a desired depth into live bone. These vibrations are forced and responsive to a time-varying disturbance from an oscillation engine or the like applied, directly or indirectly, to a structure (e.g., a prosthesis or other implant) to be installed. The disturbance can be a periodic input, a steady-state input, a transient input, and/or a random input. A periodic input may include a harmonic or non-harmonic disturbance. Oscillation about the equilibrium point may be different, or similar, for each degree of freedom available for the vibratory motion. For example, there may be one oscillation profile longitudinally and a second oscillation profile laterally (e.g., perpendicular to the longitudinal axis), the two profiles generally matching, related, derived, or independent. An amount of displacement of an oscillation is generally less than a dimension of the implant, and may be much less, on the order of about a millimeter or less.

As used herein, the term "ultrasonic" refers to a vibration in which at least one oscillation component operates at a frequency greater than about 20 kHz, and more specifically in a range of 20 kHz to 2-3 GHz, and in some instances in a range of about 20 kHz to about 200 kHz The following description relates to improvements in a wide-range of prostheses installations into live bones of patients of surgeons. The following discussion focuses primarily on total hip replacement (THR) in which an acetabular cup prosthesis is installed into the pelvis of the patient. This cup is complementary to a ball and stem (i.e., a femoral prosthesis) installed into an end of a femur engaging the acetabulum undergoing repair.

As noted in the background, the surgeon prepares the surface of the hipbone which includes attachment of the acetabular prosthesis to the pelvis. Conventionally, this attachment includes a manual implantation in which a mallet is used to strike a tamp that contacts some part of the acetabular prosthesis. Repeatedly striking the tamp drives the acetabular prosthesis into the acetabulum. Irrespective of whether current tools of computer navigation, fluoroscopy, and robotics (and other intra-operative measuring tools) have been used, it is extremely unlikely that the acetabular prosthesis will be in the correct orientation once it has been seated to the proper depth by the series of hammer strikes. After manual implantation in this way, the surgeon then may apply a series of adjusting strikes around a perimeter of the acetabular prosthesis to attempt to adjust to the desired orientation. Currently such post-impaction result is accepted as many surgeons believe that post-impaction adjustment creates an unpredictable and unreliable change which does not therefore warrant any attempts for post-impaction adjustment.

In most cases, any and all surgeons including an inexperienced surgeon may not be able to achieve the desired orientation of the acetabular prosthesis in the pelvis by conventional solutions due to unpredictability of the orientation changes responsive to these adjusting strikes. As noted above, it is most common for any surgeon to avoid post-impaction adjustment as most surgeons understand that they do not have a reliable system or method for improving any particular orientation and could easily introduce more/greater error. The computer navigation systems, fluoroscopy, and other measuring tools are able to provide the surgeon with information about the current orientation of the prosthesis (in real time) during an operation and after the prosthesis has been installed and its deviation from the desired orientation, but the navigation systems (and others) do not protect against torsional forces created by the implanting/positioning strikes. The prosthesis will find its own position in the acetabulum based on the axial and torsional forces created by the blows of the mallet. Even those navigation systems used with robotic systems (e.g., MAKO) that attempt to secure an implant in the desired orientation prior to impaction are not guaranteed to result in the installation of the implant at the desired orientation because the actual implanting forces are applied by a surgeon swinging a mallet to manually strike the tamp.

A Behzadi Medical Device (BMD) is herein described and enabled that eliminates this crude method (i.e., mallet, tamp, and surgeon-applied mechanical implanting force) of the prosthesis (e.g., the acetabular cup). A surgeon using the BMD is able to insert the prosthesis exactly where desired with proper force, finesse, and accuracy. Depending upon implementation details, the installation includes insertion of the prosthesis into patient bone, within a desired threshold of metrics for insertion depth and location) and may also include, when appropriate and/or desired, positioning at a desired orientation with the desired threshold further including metrics for insertion orientation). The use of the BMD reduces risks of fracturing and/or shattering the bone receiving the prosthesis and allows for rapid, efficient, and accurate (atraumatic) installation of the prosthesis. The BMD provides a viable interface for computer navigation assistance (also useable with all intraoperative measuring tools including fluoroscopy) during the installation as a lighter more responsive touch may be used.

The BMD encompasses many different embodiments for installation and/or positioning of a prosthesis and may be adapted for a wide range of prostheses in addition to installation and/or positioning of an acetabular prosthesis during THR.

Figure 2:
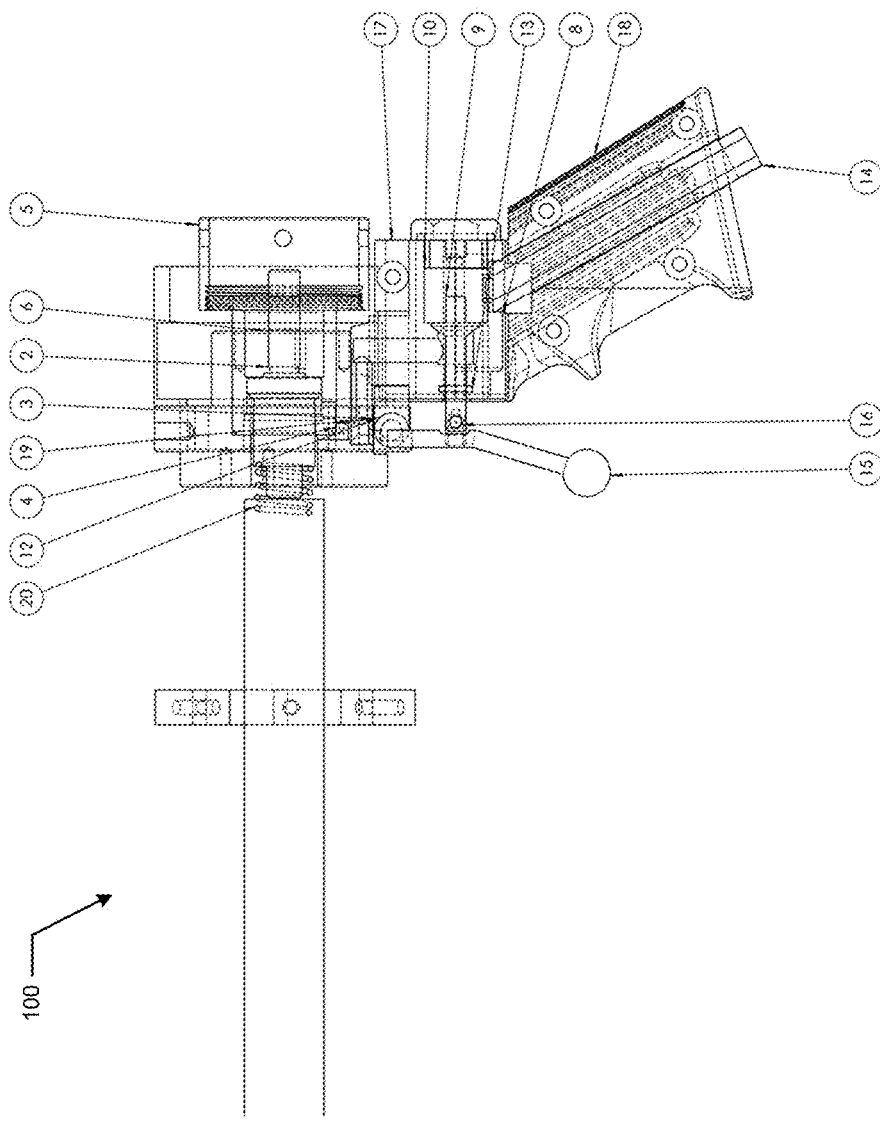
FIG. 2 illustrates a right-hand detail of the installation gun of FIG. 1.
Figure 3:
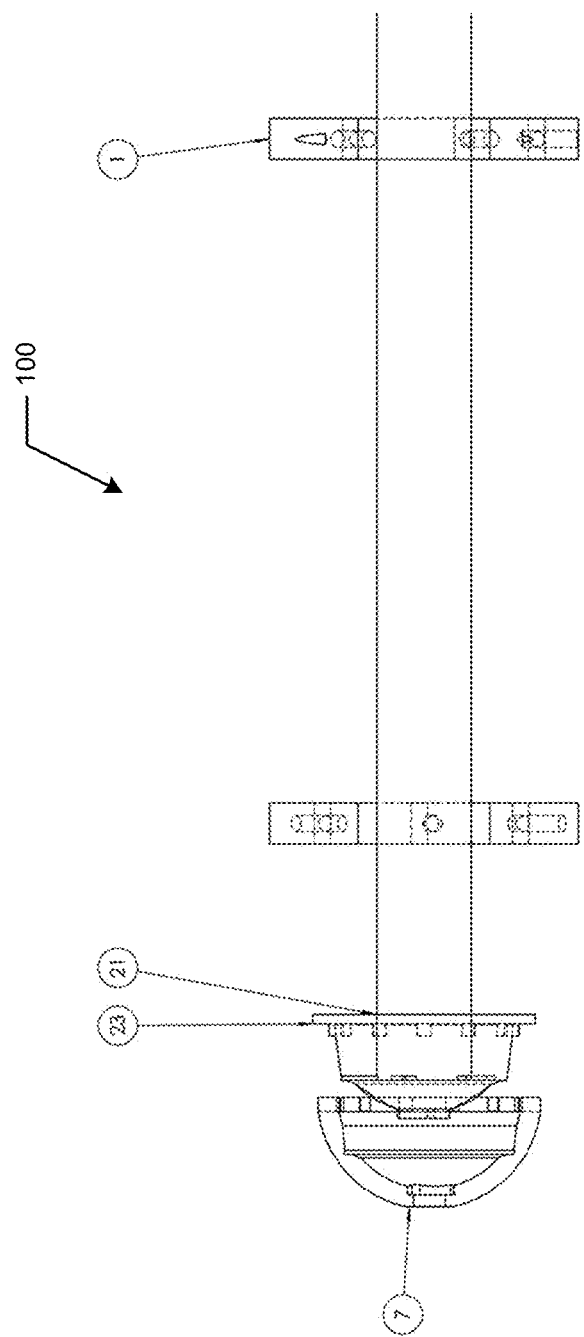
FIG. 3 illustrates a left-hand detail of the installation gun of FIG. 1 and generally when combined with FIG. 2 produces the illustration of FIG. 1.

FIG. 1 illustrates a representative installation gun 100; FIG. 2 illustrates a right-hand detail of the installation gun 100; and FIG. 3 illustrates a left-hand detail of installation gun of 100 and generally when combined with FIG. 2 produces the illustration of FIG. 1. Installation gun 100 is represented as operable using pneumatics, though other implementations may use other mechanisms for creating a desired vibratory motion of prosthesis to be installed.

Installation gun 100 is used to control precisely one or both of (i) insertion, and (ii) abduction and anteversion angles of a prosthetic component. Installation gun 100 preferably allows both installation of an acetabular cup into an acetabulum at a desired depth and orientation of the cup for both abduction and anteversion to desired values. The following reference numbers in Table I refer to elements identified in FIG. 1-FIG. 3:

TABLE I

| Device 100 Elements | |
|---|---|
| 102 | Middle guide housing |
| 104 | Klip |
| 106 | Kuciste |
| 108 | CILINDAR |
| 110 | Cjev |
| 112 | Poklopac |
| 114 | 54 mm acetabular cup |
| 116 | Body |
| 118 | Valve |
| 120 | Bottom cap |
| 122 | Upper guide housing |
| 124 | Handle cam |
| 126 | DIN 3771 6 × 1,8-N-NBR 70 |
| 128 | Main Air Inlet-Input Tube |
| 130 | Trigger |
| 132 | Trigger pin |
| 134 | DIN 3771 6 × 1,8-N-NBR 70 |
| 136 | MirrorAR15-Hand Grip 1 |
| 138 | Crossover Tube |
| 140 | 9657K103 compression spring |
| 142 | Elongate tube |
| 144 | Lower guide housing |
| 146 | Primary adapter |
| 148 | Housing |

Installation gun 100 includes a controller with a handle supporting an elongate tube 142 that terminates in adapter 146 that engages cup 114. Operation of trigger 130 initiates a motion of elongate tube 142. This motion is referred to herein as an installation force and/or installation motion that is much less than the impact force used in a conventional replacement process. An exterior housing 148 allows the operator to hold and position prosthesis 114 while elongate tube 142 moves within. Some embodiments may include a handle or other grip in addition to or in lieu of housing 148 that allows the operator to hold and operate installation gun 100 without interfering with the mechanism that provides a direct transfer of installation motion to prosthesis 114. The illustrated embodiment includes prosthesis 114 held securely by adapter 146 allowing a tilting and/or rotation of gun 100 about any axis to be reflected in the position/orientation of the secured prosthesis.

The installation motion includes constant, cyclic, periodic, and/or random motion (amplitude and/or frequency) that allows the operator to install cup 114 into the desired position (depth and orientation) without application of an impact force. There may be continuous movement or oscillations in one or more of six degrees of freedom including translation(s) and/or rotation(s) of adapter 146 about the X, Y, Z axes (e.g., oscillating translation(s) and/or oscillating/continuous rotation(s) which could be different for different axes such as translating back and forth in the direction of the longitudinal axis of the central support while rotating continuously around the longitudinal axis). This installation motion may include continuous or intermittent very high frequency movements and oscillations of small amplitude that allow the operator to easily install the prosthetic component in the desired location, and preferably also to allow the operator to also set the desired angles for abduction and anteversion.

In some implementations, the controller includes a stored program processing system that includes a processing unit that executes instructions retrieved from memory. Those instructions could control the selection of the motion parameters autonomously to achieve desired values for depth, abduction and anteversion entered into by the surgeon or by a computer aided medical computing system such as the computer navigation system. Alternatively those instructions could be used to supplement manual operation to aid or suggest selection of the motion parameters.

For more automated systems, consistent and unvarying motion parameters are not required and it may be that a varying dynamic adjustment of the motion parameters better conform to an adjustment profile of the cup installed into the acetabulum and status of the installation. An adjustment profile is a characterization of the relative ease by which depth, abduction and anteversion angles may be adjusted in positive and negative directions. In some situations these values may not be the same and the installation gun could be enhanced to adjust for these differences. For example, a unit of force applied to pure positive anteversion may adjust anteversion in the positive direction by a first unit of distance while under the same conditions that unit of force applied to pure negative anteversion may adjust anteversion in the negative direction by a second unit of distance different from the first unit. And these differences may vary as a function of the magnitude of the actual angle(s). For example, as the anteversion increases it may be that the same unit of force results in a different responsive change in the actual distance adjusted. The adjustment profile when used helps the operator when selecting the actuators and the impact force(s) to be applied. Using a feedback system of the current real-time depth and orientation enables the adjustment profile to dynamically select/modify the motion parameters appropriately during different phases of the installation. One set of motion parameters may be used when primarily setting the depth of the implant and then another set used when the desired depth is achieved so that fine tuning of the abduction and anteversion angles is accomplished more efficiently, all without use of impact forces in setting the depth and/or angle adjustment(s).

This device better enables computer navigation as the installation/adjustment forces are reduced as compared to the impacting method. This makes the required forces more compatible with computer navigation systems used in medical procedures which do not have the capabilities or control systems in place to actually provide impacting forces for seating the prosthetic component. And without that, the computer is at best relegated to a role of providing after-the-fact assessments of the consequences of the surgeon's manual strikes of the orthopedic mallet. (Also provides information before and during the impaction. It is a problem that the very act of impaction introduces variability and error in positioning and alignment of the prosthesis.

Figure 4:
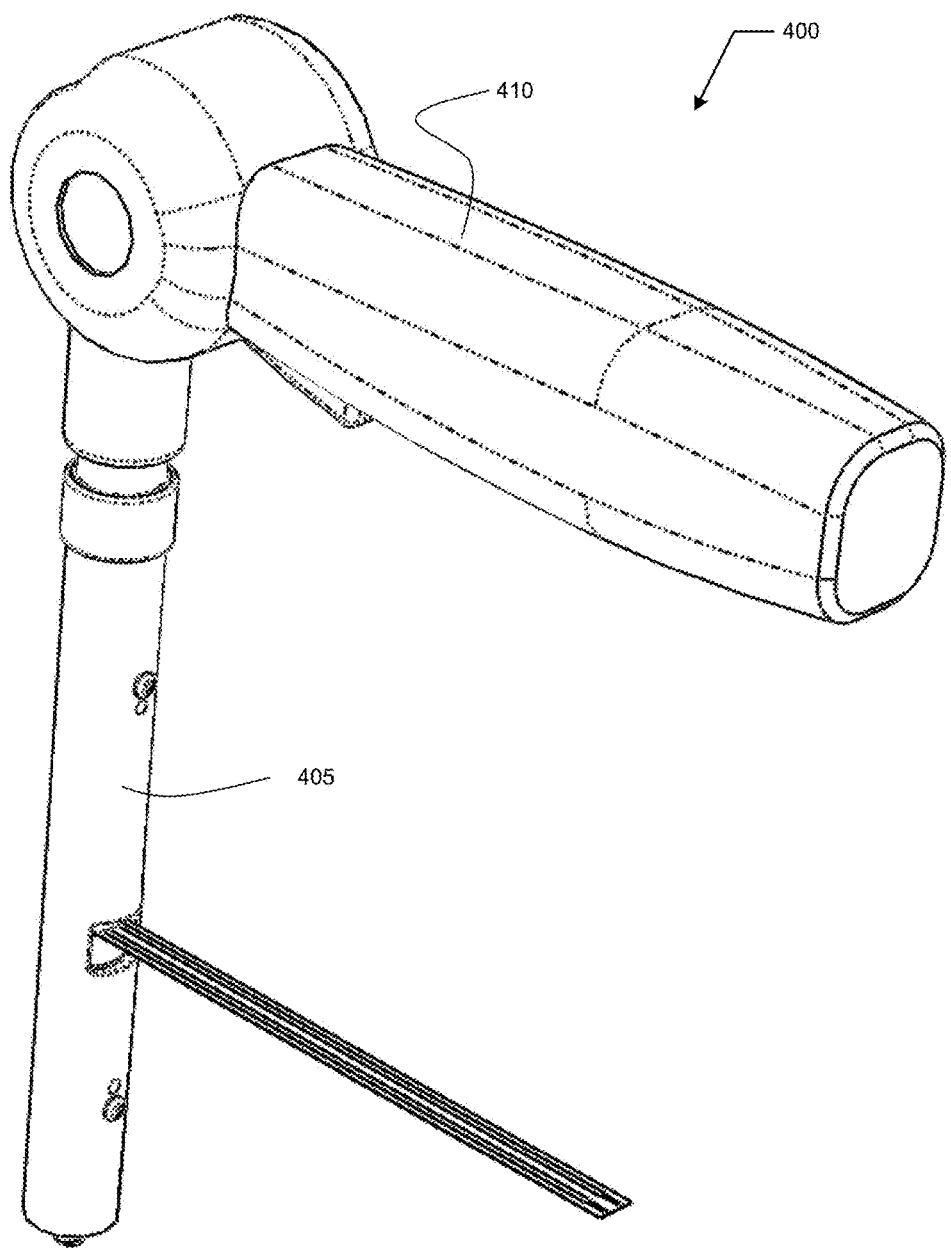
FIG. 4 illustrates a second representative installation system.
Figure 5:
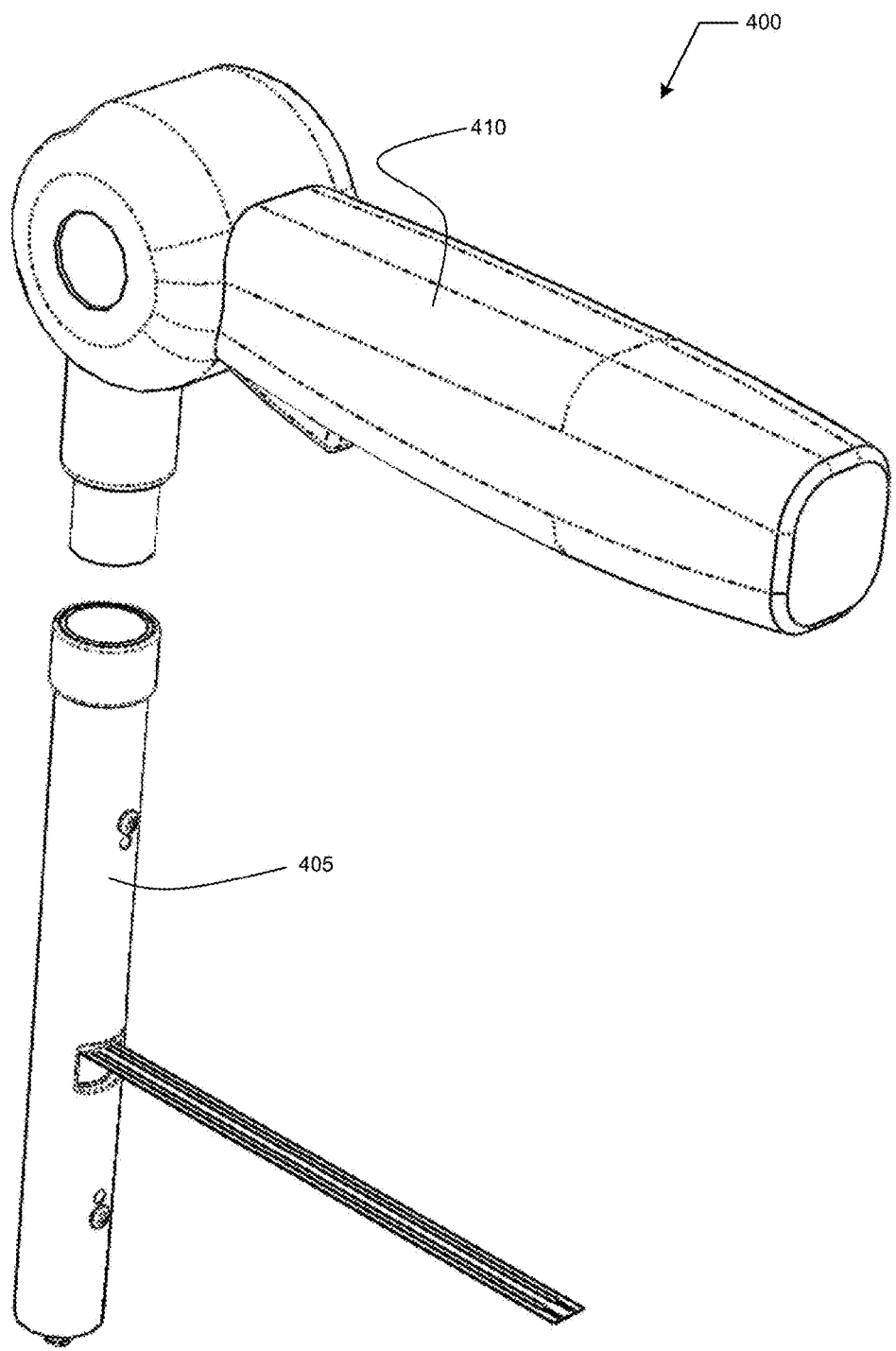
FIG. 5 illustrates a disassembly of the second representative installation system of FIG. 4.
Figure 6:
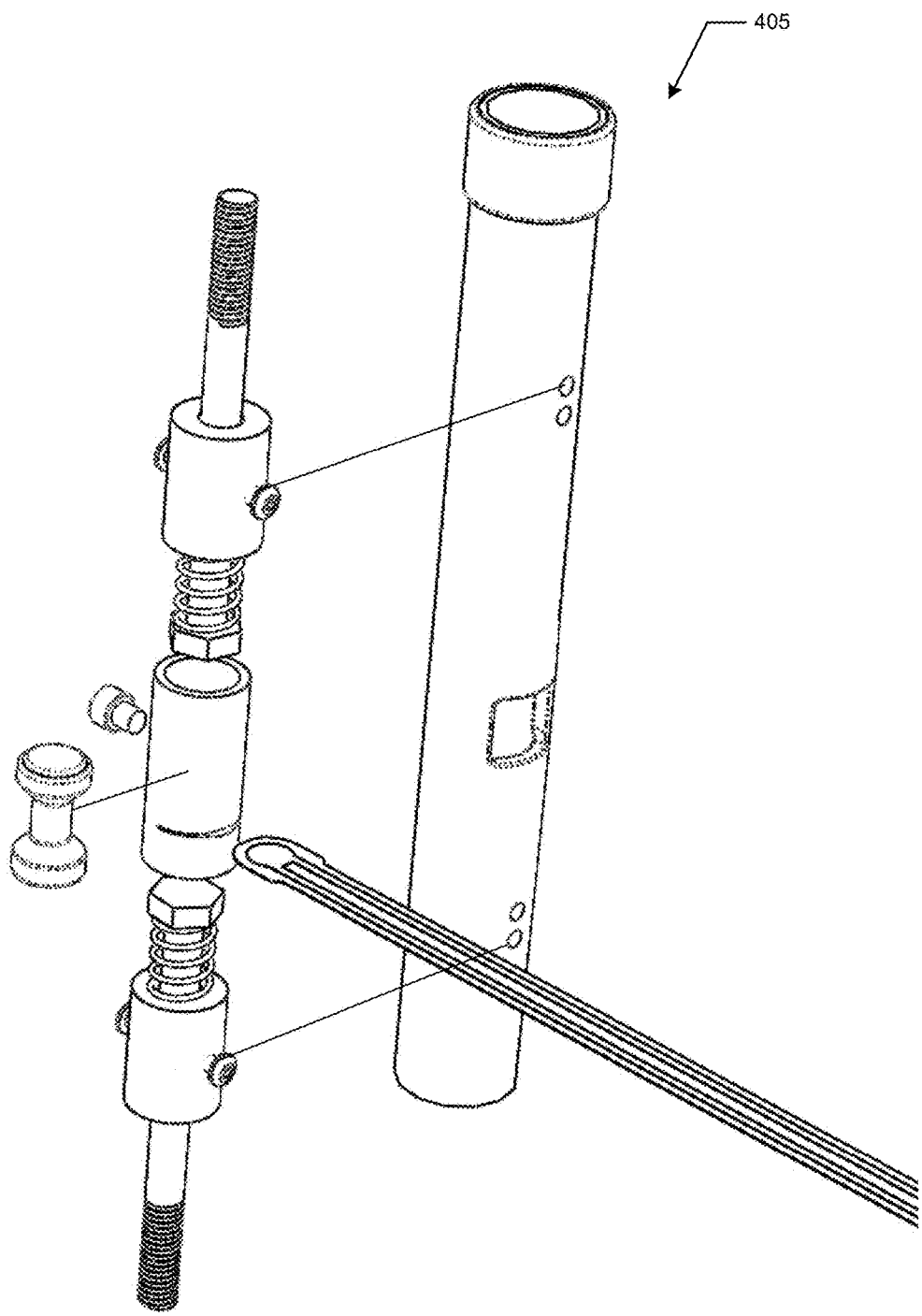
FIG. 6 illustrates a first disassembly view of the pulse transfer assembly of the installation system of FIG. 4.
Figure 7:
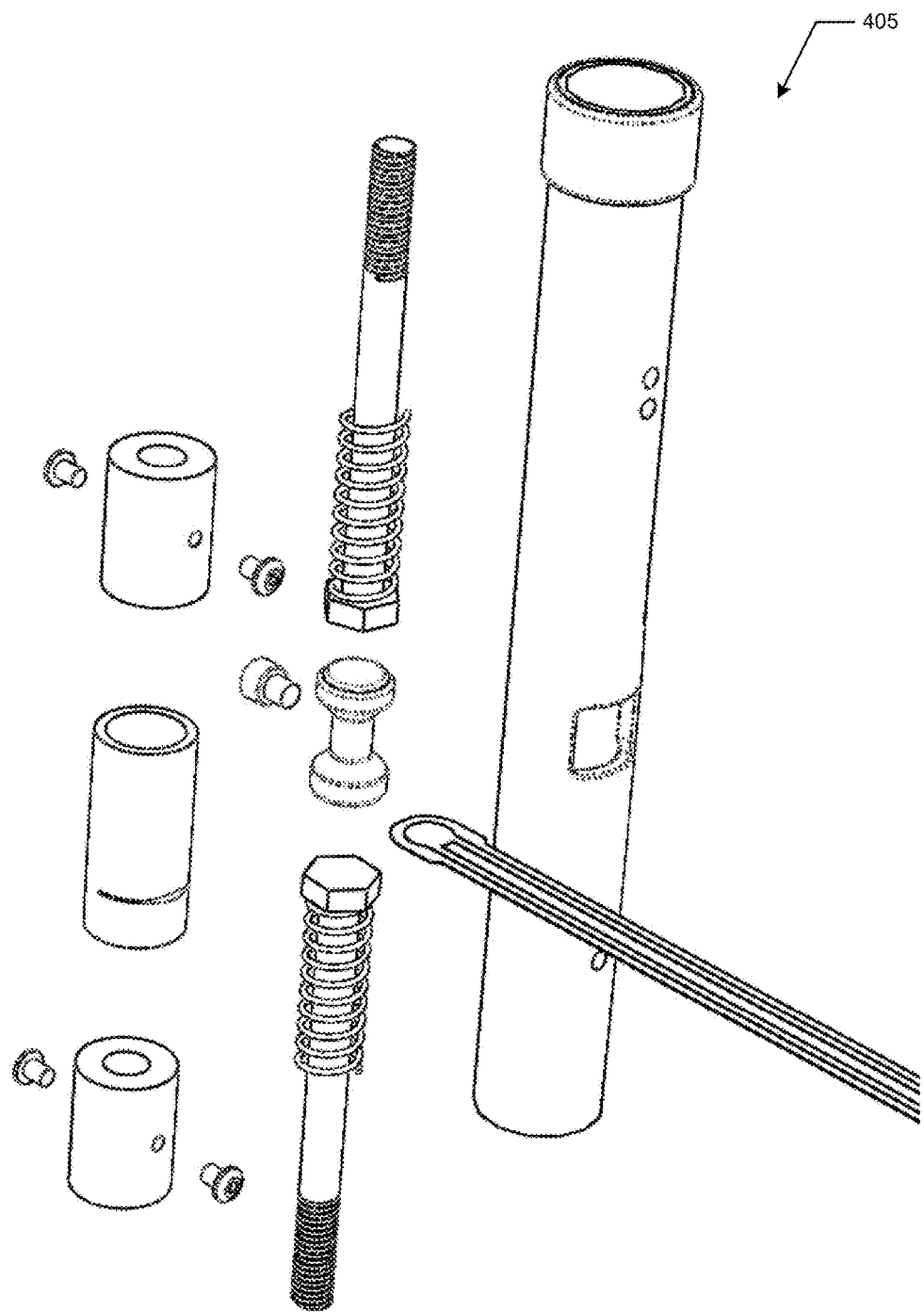
FIG. 7 illustrates a second disassembly view of the pulse transfer assembly of the installation system of FIG. 4.

FIG. 4 illustrates a second representative installation system 400 including a pulse transfer assembly 405 and an oscillation engine 410; FIG. 5 illustrates a disassembly of second representative installation system 400; FIG. 6 illustrates a first disassembly view of pulse transfer assembly 405; and FIG. 7 illustrates a second disassembly view of pulse transfer assembly 405 of installation system 400.

Installation system 400 is designed for installing a prosthesis that, in turn, is configured to be implanted into a portion of bone at a desired implantation depth. The prosthesis includes some type of attachment system (e.g., one or more threaded inserts, mechanical coupler, link, or the like) allowing the prosthesis to be securely and rigidly held by an object such that a translation and/or a rotation of the object about any axis results in a direct corresponding translation and/or rotation of the secured prosthesis.

Oscillation engine 410 includes a controller coupled to a vibratory machine that generates an original series of pulses having a generation pattern. This generation pattern defines a first duty cycle of the original series of pulses including one or more of a first pulse amplitude, a first pulse direction, a first pulse duration, and a first pulse time window. This is not to suggest that the amplitude, direction, duration, or pulse time window for each pulse of the original pulse series are uniform with respect to each other. Pulse direction may include motion having any of six degrees of freedom—translation along one or more of any axis of three orthogonal axes and/or rotation about one or more of these three axes. Oscillation engine 410 includes an electric motor powered by energy from a battery, though other motors and energy sources may be used.

Pulse transfer assembly 405 includes a proximal end 415 coupled to oscillation engine 410 and a distal end 420, spaced from proximal end 420, coupled to the prosthesis using a connector system 425. Pulse transfer assembly 405 receives the original series of pulses from oscillation engine 410 and produces, responsive to the original series of pulses, an installation series of pulses having an installation pattern. Similar to the generation pattern, the installation pattern defines a second duty cycle of the installation series of pulses including a second pulse amplitude, a second pulse direction, a second pulse duration, and a second pulse time window. Again, this is not to suggest that the amplitude, direction, duration, or pulse time window for each pulse of the installation pulse series are uniform with respect to each other. Pulse direction may include motion having any of six degrees of freedom—translation along one or more of any axis of three orthogonal axes and/or rotation about one or more of these three axes.

For some embodiments of pulse transfer assembly 405, the installation series of pulses will be strongly linked to the original series and there will be a close match, if not identical match, between the two series. Some embodiments may include a more complex pulse transfer assembly 405 that produces an installation series that is more different, or very different, from the original series.

Connector system 425 (e.g., one or more threaded studs complementary to the threaded inserts of the prosthesis, or other complementary mechanical coupling system) is disposed at proximal end 420. Connector system 425 is configured to secure and rigidly hold the prosthesis. In this way, the attached prosthesis becomes a secured prosthesis when engaged with connector system 425.

Pulse transfer assembly 405 communicates the installation series of pulses to the secured prosthesis and produces an applied series of pulses that are responsive to the installation series of pulses. Similar to the generation pattern and the installation pattern, the applied pattern defines a third duty cycle of the applied series of pulses including a third pulse amplitude, a third pulse direction, a third pulse duration, and a third pulse time window. Again, this is not to suggest that the amplitude, direction, duration, or pulse time window for each pulse of the applied pulse series are uniform with respect to each other. Pulse direction may include motion having any of six degrees of freedom—translation along one or more of any axis of three orthogonal axes and/or rotation about one or more of these three axes.

For some embodiments of pulse transfer assembly 405, the applied series of pulses will be strongly linked to the original series and/or the installation series and there will be a close, if not identical, match between the series. Some embodiments may include a more complex pulse transfer assembly 405 that produces an applied series that is more different, or very different, from the original series and/or the installation series. In some embodiments, for example one or more components may be integrated together (for example, integrating oscillation engine 410 with pulse transfer assembly 405) so that the first series and the second series, if they exist independently are nearly identical if not identical).

The applied series of pulses are designed to impart a vibratory motion to the secured prosthesis that enable an installation of the secured prosthesis into the portion of bone to within 95% of the desired implantation depth without a manual impact. That is, in operation, the original pulses from oscillation engine 410 propagate through pulse transfer assembly 405 (with implementation-depending varying levels of fidelity) to produce the vibratory motion to the prosthesis secured to connector system 425. In a first implementation, the vibratory motion allows implanting without manual impacts on the prosthesis and in a second mode an orientation of the implanted secured prosthesis may be adjusted by rotations of installation system 400 while the vibratory motion is active, also without manual impact. In some implementations, the pulse generation may produce different vibratory motions optimized for these different modes.

Installation system 400 includes an optional sensor 430 (e.g., a flex sensor or the like) to provide a measurement (e.g., quantitative and/or qualitative) of the installation pulse pattern communicated by pulse transfer assembly 405. This measurement may be used as part of a manual or computerized feedback system to aid in installation of a prosthesis. For example, in some implementations, the desired applied pulse pattern of the applied series of pulses (e.g., the vibrational motion of the prosthesis) may be a function of a particular installation pulse pattern, which can be measured and set through sensor 430. In addition to, or alternatively, other sensors may aid the surgeon or an automated installation system operating installation system 400, such as a bone density sensor or other mechanism to characterize the bone receiving the prosthesis to establish a desired applied pulse pattern for optimal installation.

The disassembled views of FIG. 6 and FIG. 7 detail a particular implementation of pulse transfer assembly 405, it being understood that there are many possible ways of creating and communicating an applied pulse pattern responsive to a series of generation pulses from an oscillation engine. The illustrated structure of FIG. 6 and FIG. 7 generate primarily longitudinal/axial pulses in response to primarily longitudinal/axial generation pulses from oscillation engine 410.

Pulse transfer assembly 405 includes an outer housing 435 containing an upper transfer assembly 640, a lower transfer assembly 645 and a central assembly 650. Central assembly 650 includes a double anvil 655 that couples upper transfer assembly 640 to lower transfer assembly 645. Outer housing 635 and central assembly 650 each include a port allowing sensor 630 to be inserted into central assembly 650 between an end of double anvil 655 and one of the upper/lower transfer assemblies.

Upper transfer assembly 640 and lower transfer assembly 645 each include a support 660 coupled to outer housing 435 by a pair of connectors. A transfer rod 665 is moveably disposed through an axial aperture in each support 660, with each transfer rod 665 including a head at one end configured to strike an end of double anvil 655 and a coupling structure at a second end. A compression spring 670 is disposed on each transfer rod 665 between support 660 and the head. The coupling structure of upper transfer assembly 640 cooperates with oscillation engine 410 to receive the generated pulse series. The coupling structure of lower transfer assembly 645 includes connector system 425 for securing the prosthesis. Some embodiments may include an adapter, not shown, that adapts connector system 425 to a particular prosthesis, different adapters allowing use of pulse transfer assembly 405 with different prosthesis.

Central assembly 650 includes a support 675 coupled to outer housing 435 by a connector and receives double anvil 655 which moves freely within support 675. The heads of the upper transfer assembly and the lower transfer assembly are disposed within support 675 and arranged to strike corresponding ends of double anvil 655 during pulse generation.

In operation, oscillation engine 410 generates pulses that are transferred via pulse transfer assembly 405 to the prosthesis secured by connector system 425. The pulse transfer assembly 405, via upper transfer assembly 640, receives the generated pulses using transfer rod 665. Transfer rod 665 of upper transfer assembly 640 moves within support 660 of upper transfer assembly 640 to communicate pulses to double anvil 655 moving within support 675. Double anvil 655, in turn, communicates pulses to transfer rod 665 of lower transfer assembly 645 to produce vibratory motion of a prosthesis secured to connector system 425. Transfer rods 665 move, in this illustrated embodiment, primarily longitudinally/axially within outer housing 435 (a longitudinal axis defined as extending between proximate end 415 and distal end 420. In this way, the surgeon may use outer housing 435 as a hand hold when installing and/or positioning the vibrating prosthesis.

The use of discrete transfer portions (e.g., upper, central, and lower transfer assemblies) for pulse transfer assembly 405 allows a form of loose coupling between oscillation engine 410 and a secured prosthesis. In this way pulses from oscillation engine 410 are converted into a vibratory motion of the prosthesis as it is urged into the bone during operation. Some embodiments may provide a stronger coupling by directly securing one component to another, or substituting a single component for a pair of components.

Figure 8:
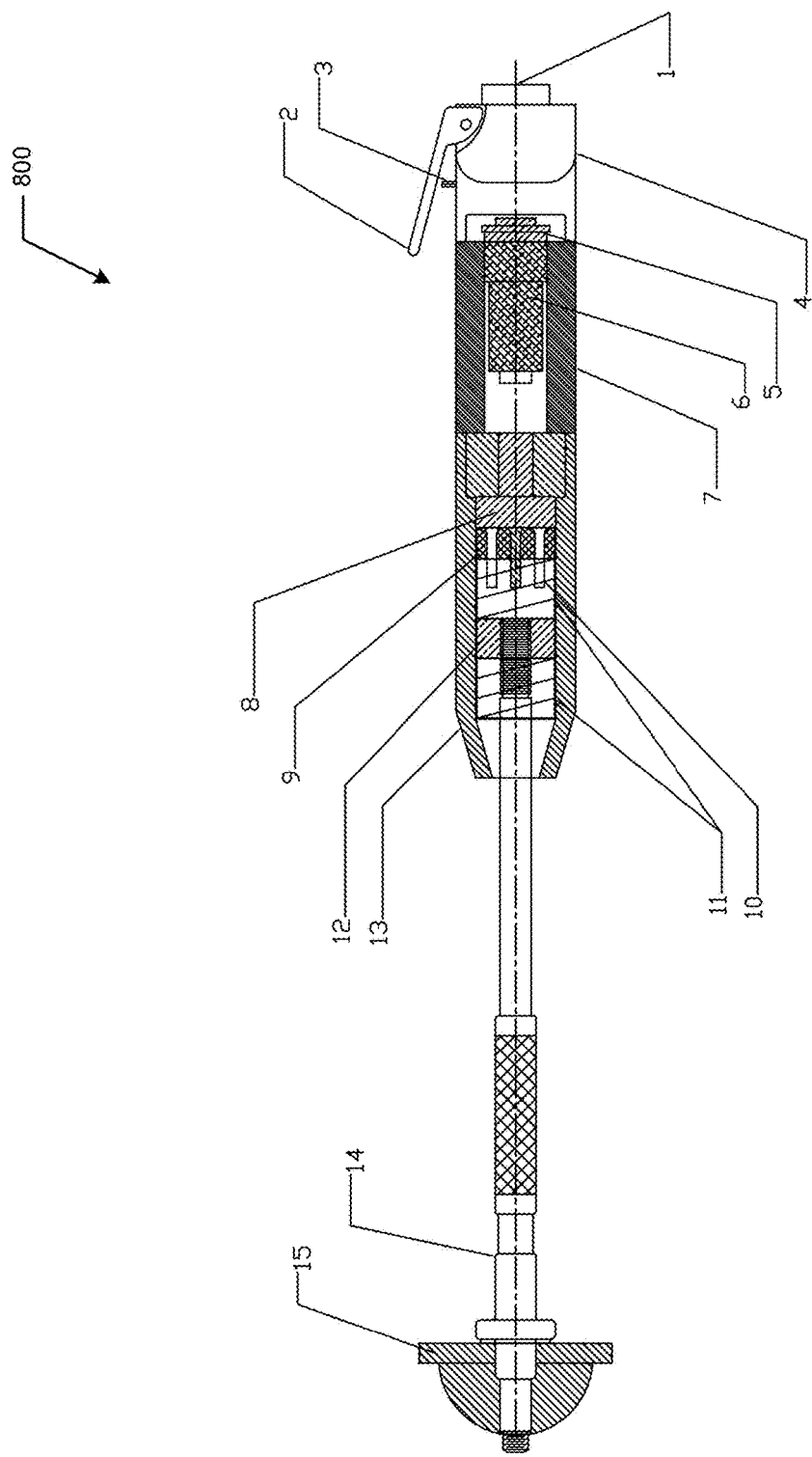
FIG. 8 illustrates a third representative installation system.
Figure 9:
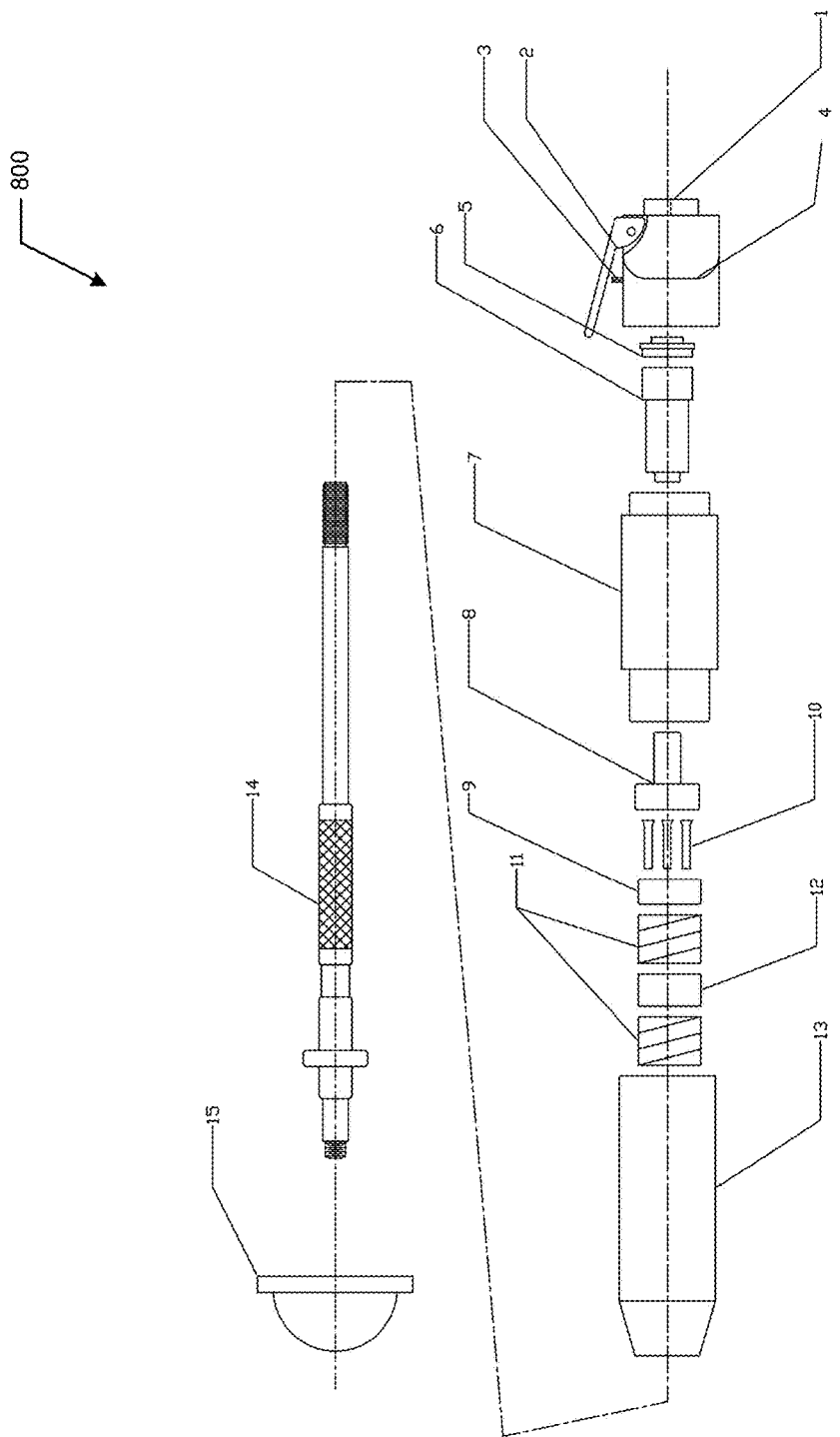
FIG. 9 illustrates a disassembly view of the third representative installation system of FIG. 8.

FIG. 8 illustrates a third representative installation system 800; and FIG. 9 illustrates a disassembly view of third representative installation system 800.

The embodiments of FIG. 4-FIG. 8 have demonstrated insertion of a prosthetic cup into a bone substitute substrate with ease and a greatly reduced force as compared to use of a mallet and tamp, especially as no impaction was required. While the insertion was taking place and vibrational motion was present at the prosthesis, the prosthesis could be positioned with relative ease by torqueing on a handle/outer housing to an exact desired alignment/position. The insertion force is variable and ranges between 20 to 800 pounds of force. Importantly the potential for use of significantly smaller forces in application of the prosthesis (in this case the acetabular prosthesis) in bone substrate with the present invention is demonstrated to be achievable.

Similarly to installation system 100 and installation system 400, installation system 800 is used to control precisely one or both of (i) installation and (ii) abduction and anteversion angles of a prosthetic component. Installation system 800 preferably allows both installation of an acetabular cup into an acetabulum at a desired depth and orientation of the cup for both abduction and anteversion to desired values. The following reference numbers in Table II refer to elements identified in FIG. 8-FIG. 9:

TABLE II

| Device 800 Elements | |
| --- | --- |
| 802 | Air Inlet |
| 804 | Trigger |
| 806 | Needle Valve |
| 808 | Valve Body |
| 810 | Throttle Cap |
| 812 | Piston |
| 814 | Cylinder |
| 816 | Driver |
| 818 | Needle Block |
| 820 | Needles |
| 822 | Suspension Springs |
| 824 | Anvil |
| 826 | Nozzle |
| 828 | Connector Rod |
| 830 | Prosthesis (e.g., acetabular cup) |

Installation system 800 includes a controller with a handle supporting an elongate rod that terminates in a connector system that engages prosthesis 830. Operation of trigger 804 initiates a motion of the elongate rod. This motion is referred to herein as an installation force and/or installation motion that is much less than the impact force used in a conventional replacement process. An exterior housing allows the operator to hold and position prosthesis 830 while the elongate rod moves within. Some embodiments may include a handle or other grip in addition to or in lieu of the housing that allows the surgeon operator to hold and operate installation system 800 without interfering with the mechanism that provides a direct transfer of installation motion. The illustrated embodiment includes prosthesis 830 held securely allowing a tilting and/or rotation of installation system about any axis to be reflected in the position/orientation of the secured prosthesis.

The actuator is pneumatically operated oscillation device that provides the impact and vibration action this device uses to set the socket (it being understand that alternative motive systems may be used in addition to, or alternatively to, a pneumatic system). Alternatives including mechanical and/or electromechanical systems, motors, and/or engines. The actuator includes air inlet port 802, trigger 804, needle valve 806, cylinder 814, and piston 812.

Air is introduced through inlet port 802 and as trigger 804 is squeezed needle valve 806 admits air into the cylinder 814 pushing piston 812 to an opposing end of cylinder 814. At the opposite end piston 812 opens a port allowing the air to be admitted and pushing the piston 812 back to the original position.

This action provides the motive power for operation of the device and functions in this embodiment at up to 70 Hz. The frequency can be adjusted by trigger 804 and an available air pressure at air inlet port 802.

As piston 812 impacts driver 816, driver 816 impacts needles 820 of needle block 818. Needles 820 strike anvil 824 which is directly connected to prosthesis 830 via connecting rod 828.

Suspension springs 822 provide a flexibility to apply more or less total force. This flexibility allows force to be applied equally around prosthesis 830 or more force to one side of prosthesis 830 in order to locate prosthesis 830 at an optimum/desired orientation. Installation system 800 illustrates a BMD having a more strongly coupled pulse transfer system between an oscillation engine and prosthesis 830.

The nature and type of coupling of pulse communications between the oscillation engine and the prosthesis may be varied in several different ways. For example, in some implementations, needles 820 of needle block 818 are independently moveable and respond differently to piston 812 motion. In other implementations, the needles may be fused together or otherwise integrated together, while in other implementations needles 820 and needle block 818 may be replaced by an alternative cylinder structure.

As illustrated, while installation embodiments provide for a primarily longitudinal implementation, installation system 800 includes a design feature intended to allow the inserting/vibratory force to be "steered" by applying forces to be concentrated on one side or another of the prosthesis. Implementations that produce a randomized vibrational motion, including "lateral" motion components in addition to, or in lieu of, the primarily longitudinal vibrational motion of the disclosed embodiments may be helpful for installation of prosthesis in a wide range of applications including THR surgery.

Installation system 400 and installation system 800 included an oscillation engine producing pulses at approximately 60 Hz. System 400 operated at 60 Hz while system 800 was capable of operating at 48 to 68 Hz. In testing, approximately 4 seconds of operation resulted in a desired insertion and alignment of the prosthesis (meaning about 240 cycles of the oscillation engine). Conventional surgery using a mallet striking a tamp to impact the cup into place is generally complete after 10 blows of the mallet/hammer.

Figure 10:
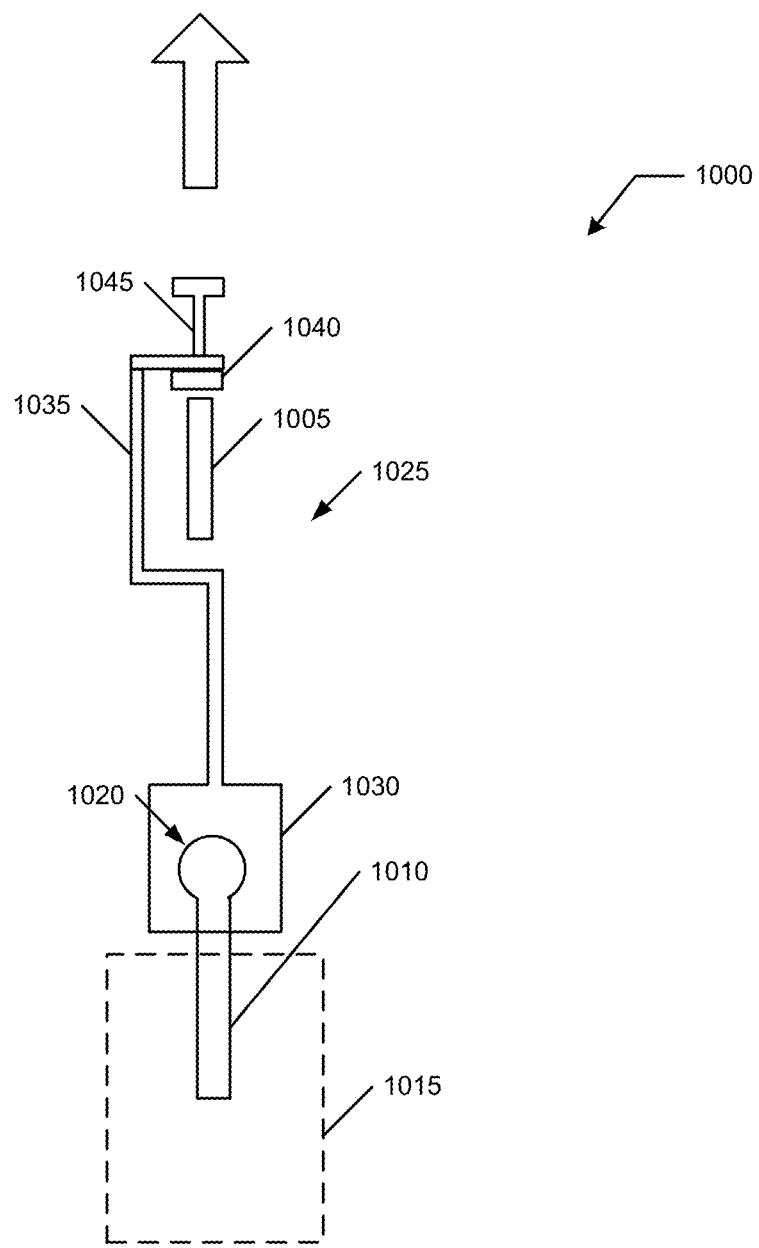
FIG. 10 illustrates a system illustrating use of tool for extraction of a prosthesis.

FIG. 10 illustrates a system 1000 illustrating use of a tool 1005 for extraction of a prosthesis 1010 bonded within a portion of live bone 1015. Bonded prosthesis 1010 includes an exposed portion 1020. Tool 1005 may include a version of a BMD tool as described herein or other non-impacting tool capable of producing extractive forces/pulses/vibrations (which may include mechanical ultrasonic patterns).

Tool 1005 cooperates with, or is integrated into, a mechanical assembly 1025 that includes an adaptor portion 1030 to mechanically engage exposed portion 1020. There are many ways to implement mechanical assembly 1025 to communicate extraction forces/pulses from tool 1005 to bonded prosthesis 1010 through the mechanical coupling to exposed portion 1020.

System 1000 includes one particular implementation for mechanical assembly 1025 to facilitate one description of an embodiment of the present invention. Mechanical assembly 1025 includes a C-portion 1035 coupled to adaptor portion 1030, the C-portion including a pair of lateral legs coupled to opposite ends of a longitudinal leg generally parallel to an extraction path intended for bonded prosthesis 1010 during extraction. One of the lateral legs includes an adaptor portion 1040 for engaging tool 1005 allowing tool 1005 to transfer extraction force(s)/pulses to bonded prosthesis 1010.

In some embodiments, the mechanical coupling of adaptor portion 1030 to exposed portion 1020 is such that vibratory pulses/excitement produced by tool 1005 and communicated by mechanical assembly 1025 are able to be communicated to bonded prosthesis 1010 to produce a vibrating/oscillating bonded prosthesis 1010 as an aid in extraction, sometimes the vibration is applied while concurrently applying a force withdrawing prosthesis from the portion of bone. This is in contrast to any system which simply applied a vibratory to a bonded structure with a goal of breaking up a cured bonding agent securing the structure in place.

Mechanical assembly 1025 may include an optional handle 1045 to aid the surgeon/operator when extracting bonded prosthesis 1010 from bone portion 1015 in response to extractive impulses provided by tool 1005.

Experimental

Both system 400 and system 800 were tested in a bone substitute substrate with a standard Zimmer acetabular cup using standard technique of under reaming a prepared surface by 1 mm and inserting a cup that was one millimeter larger. The substrate was chosen as the best option available to us to study this concept, namely a dense foam material. It was recognized that certain properties of bone would not be represented here (e.g. an ability of the substrate to stretch before failure).

Both versions demonstrated easy insertion and positioning of the prosthetic cup within the chosen substrate. We were able to move the cup in the substrate with relative ease. There was no requirement for a mallet or hammer for application of a large impact. These experiments demonstrated that the prosthetic cups could be inserted in bone substitute substrates with significantly less force and more control than what could be done with blows of a hammer or mallet. We surmise that the same phenomena can be reproduced in human bone. We envision the prosthetic cup being inserted with ease with very little force.

Additionally we believe that simultaneously, while the cup is being inserted, the position of the cup can be adjusted under direct visualization with any intra-operative measurement system (navigation, fluoroscopy, etc.). This invention provides a system that allows insertion of a prosthetic component with NON-traumatic force (insertion) as opposed to traumatic force (impaction).

Experimental Configuration—System 400

Oscillation engine 410 included a Craftsman G2 Hammerhead nailer used to drive fairly large framing nails into wood in confined spaces by applying a series of small impacts very rapidly in contrast to application of few large impacts.

The bone substitute was 15 pound density urethane foam to represent the pelvic acetabulum. It was shaped with a standard cutting tool commonly used to clean up a patient's damaged acetabulum. A 54 mm cup and a 53 mm cutter were used in testing.

In one test, the cup was inserted using a mallet and tamp, with impaction complete after 7 strikes. Re-orientation of the cup was required by further strikes on a periphery of the cup after impaction to achieve a desired orientation. It was qualitatively determined that the feel and insertion were consistent with impaction into bone.

An embodiment of system 400 was used in lieu of the mallet and tamp method. Several insertions were performed, with the insertions found to be much more gradual; allowing the cup to be guided into position (depth and orientation during insertion). Final corrective positioning is easily achievable using lateral hand pressure to rotate the cup within the substrate while power was applied to the oscillation engine.

Further testing using the sensor included general static load detection done to determine the static (non-impact) load to push the cup into the prepared socket model. This provided a baseline for comparison to the impact load testing. The prosthesis was provided above a prepared socket with a screw mounted to the cup to transmit a force applied from a bench vise. The handle of the vice was turned to apply an even force to compress the cup into the socket until the cup was fully seated. The cup began to move into the socket at about an insertion force of ~200 pounds and gradually increased as diameter of cup inserted into socket increased to a maximum of 375 pounds which remained constant until the cup was fully seated.

Installation system 400 was next used to install the cup into a similarly prepared socket. Five tests were done, using different frame rates and setup procedures, to determine how to get the most meaningful results. All tests used a 54 mm acetabular Cup. The oscillation engine ran at an indicated 60 impacts/second. The first two tests were done at 2,000 frames/second, which wasn't fast enough to capture all the impact events, but helped with designing the proper setup. Test 3 used the oscillation engine in an already used socket, 4,000 frames per second. Test 4 used the oscillation engine in an unused foam socket at 53 mm, 4,000 frames per second.

Test 3: In already compacted socket, the cup was pulsed using the oscillation engine and the pulse transfer assembly. Recorded strikes between 500 and 800 lbs, with an average recorded pulse duration 0.8 ms.

Test 4: Into an unused 53 mm socket, the cup was pulsed using the oscillation engine and the pulse transfer assembly. Recorded impacts between 250 and 800 lbs, and an average recorded pulse duration 0.8 ms. Insertion completed in 3.37 seconds, 202 impact hits.

Test 5: Into an unused 53 mm socket, the cup was inserted with standard hammer (for reference). Recorded impacts between 500 and 800 lbs, and an average recorded pulse duration 22.0 ms. Insertion completed in 4 seconds using 10 impact hits for a total pressure time of 220 ms. This test was performed rapidly to complete it in 5 seconds for good comparability with tests 3 and 4 used 240 hits in 4 seconds, with a single hit duration of 0.8 ms., for a total pressure time of 192 ms.

In non-rigorous comparison testing without a direct comparison between system 400 and system 800, generally it appears that the forces used for installation using system 800 were lower than system 400 by a factor of 10. This suggests that there are certain optimizing characteristics for operation of an installation system. There are questions such as to how low these forces can be modulated and still allow easy insertion of the prosthetic cup in this model and in bone. What is the lowest force required for insertion of a prosthetic cup in to this substrate using the disclosed concepts? What is the lowest force required for insertion of a prosthetic cup into hard bone using these concepts? And what is the lowest force required for insertion of a prosthetic cup into soft and osteoporotic bone using these concepts? These are the questions that can be addressed in future phase of implementations of the present invention.

Additionally, basic studies can further be conducted to correlate a density and a porosity of bone at various ages (e.g., through a cadaver study) with an appropriate force range and vibratory motion pattern required to insert a cup using the present invention. For example a surgeon will be able to insert sensing equipment in patient bone, or use other evaluative procedures, (preoperative planning or while performing the procedure for example) to asses porosity and density of bone. Once known, the density or other bone characteristic is used to set an appropriate vibratory pattern including a force range on an installation system, and thus use a minimal required force to insert and/or position the prosthesis.

BMD is a "must have" device for all medical device companies and surgeons. Without BMD the Implantation problem is not addressed, regardless of the recent advances in technologies in hip replacement surgery (i.e.; Navigation, Fluoroscopy, MAKO/robotics, accelerometers/gyro meters, etc.). Acetabular component (cup) positioning remains the biggest problem in hip replacement surgery. Implantation is the final step where error is introduced into the system and heretofore no attention has been brought to this problem. Current technologies have brought significant awareness to the position of the implants within the pelvis during surgery, prior to impaction. However, these techniques do not assist in the final step of implantation.

BMD allows all real time information technologies to utilize (a tool) to precisely and accurately implant the acetabular component (cup) within the pelvic acetabulum. BMD device coupled with use of navigation technology and fluoroscopy and (other novel measuring devices) is the only device that will allow surgeons from all walks of life, (low volume/high volume) to perform a perfect hip replacement with respect to acetabular component (cup) placement. With the use of BMD, surgeons can feel confident that they are doing a good job with acetabular component positioning, achieving the "perfect cup" every time. Hence the BMD concept eliminates the most common cause of complications in hip replacement surgery which has forever plagued the surgeon, the patients and the society in general.

It is known to use ultra sound devices in connection with some aspects of THR, primarily for implant removal (as some components may be installed using a cement that may be softened using ultrasound energy). There may be some suggestion that some ultrasonic devices that employ "ultrasound" energy could be used to insert a prosthesis for final fit, but it is in the context of a femoral component and it is believed that these devices are not presently actually used in the process). Some embodiments of BMD, in contrast, can simply be a vibratory device (non ultrasonic), and may not be ultrasonic and some implementations may include ultrasonic operation, and may be more profound than simply an implantation device as it is most preferably a positioning device for the acetabular component in THR. Further, there is a discussion that ultrasound devices may be used to prepare bones for implanting a prosthesis. BMD does not address preparation of the bone as this is not a primary thrust of this aspect of the present invention. Some implementations of BMD may include a similar or related feature. The forces applied by the vibration will be less than an impact force and preferably enable installation without requiring impact forces applied to the mechanism by which the equilibrium point is moved during installation of the vibrating implant. That mechanism may be hand pressure from the surgeon guiding the vibrating implant into a desired depth and orientation or may include some other mechanical application of less-than-impact force to adjust the equilibrium point. An extracting version that supplies/applies non-impactful extractive forces may be used in other contexts in addition to extracting a bonded prosthesis from a portion of bone.

Some embodiments BMD include devices that concern themselves with proper installation and positioning of the prosthesis (e.g., an acetabular component) at the time of implanting of the prosthesis. Very specifically, it uses some form of vibratory energy coupled with a variety of "real time measurement systems" to POSITION the cup in a perfect alignment with minimal use of force. A prosthesis, such as for example, an acetabular cup, resists insertion. Once inserted, the cup resists changes to the inserted orientation. The BMDs of the present invention produce an insertion vibratory motion of a secured prosthesis that reduces the forces resisting insertion. In some implementations, the BMD may produce a positioning vibratory motion that reduces the forces resisting changes to the orientation. There are some implementations that produce both types of motion, either as a single vibratory profile or alternative profiles. In the present context for purposes of the present invention, the vibratory motion is characterized as "floating" the prosthesis as the prosthesis can become much simpler to insert and/or re-orient while the desired vibratory motion is available to the prosthesis. Some embodiments are described as producing vibrating prosthesis with a predetermined vibration pattern. In some implementations, the predetermined vibration pattern is predictable and largely completely defined in advance. In other implementations, the predetermined vibration pattern includes randomized vibratory motion in one or more motion freedoms of the available degrees of freedom (up to six degrees of freedom). That is, whichever translation or rotational freedom of motion is defined for the vibrating prosthesis, any of them may have an intentional randomness component, varying from large to small. In some cases the randomness component in any particular motion may be large and in some cases predominate the motion. In other cases the randomness component may be relatively small as to be barely detectable.

During our investigation of the BMD vibrational prototype (for insertion) we discovered that the direction of these impulsive forces (vibratory patterns) can also closely controlled (i.e.: can be unidirectional or bidirectional). Our BMD prototypes have the ability to insert (push) uni-directionally, withdrawal (pull) uni-directionally, or produce a bidirectional force with varying proportions of push vs. pull. The bi-directional systems could produce higher frequencies than the unidirectional systems, and have theoretical and practical advantages in affecting frictional forces between the bone/implant, cement/bone, or broach/bone interfaces. For insertion of the cup into a substrate it was felt that unidirectional vibratory insertion (in a positive direction) is ideal. We discovered that unidirectional vibratory pattern (withdrawal) and a bidirectional vibration may have other applications such as in revision surgery, preparation of bone, and for insertion of bidirectional prosthetic cups.

Bidirectional and Unidirectional BMD vibratory tool for Revision: We have previously described the use of BMD3 for revision purposes and for the removal of prosthesis that have been already placed in bone. We believe that the revision BMD3 vibratory tool can operate in two distinct modes. The most important aspect of this tool is the fact that an oscillatory pattern is created and transferred to prosthesis fixed in bone. This oscillatory pattern can be delivered to the prosthesis in bone in one of two ways. 1. An oscillatory pulse that provides a unidirectional (pulling) vibration. 2. An oscillatory pulse that provides bidirectional vibration to an already implanted prosthesis. One or the other of these oscillatory vibrations may have better chance of loosening the prosthesis/bone, prosthesis/cement, or cement/bone interface. We believe this is a novel and new method that can be used to remove a prosthesis fixed in human bone.

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. An extraction device for a prosthesis disposed in a bone having an exposed portion, comprising:
   a controller including a trigger;
   a support having a proximal end and a distal end opposite of said proximal end, said support further having a longitudinal axis extending from said proximal end to said distal end with said proximal end coupled to said controller, said support further having an adapter coupled to said distal end with said adapter configured to engage the exposed portion of the prosthesis; and
   an oscillator coupled to said controller and to said support, said oscillator configured to control a series of vibratory pulses having an oscillation frequency and an oscillation magnitude of said support with said oscillation frequency and said oscillation magnitude configured to extract the prosthesis responsive to said series of vibratory pulses without impact forces;
   wherein said engine is operable in two distinctive selectable modes including a unidirectional mode providing only extractive forces and a bidirectional mode providing both extractive and insertional forces.

2. The extraction device of claim 1 wherein said series of vibratory pulses includes a vibratory motion having a frequency greater than or equal to about 20 kHz.

3. The extraction device of claim 1 further comprising a mechanical frame having a C-portion, said mechanical frame including said adaptor wherein said C-portion includes a pair of lateral legs coupled to opposing ends of a longitudinal leg with said longitudinal leg generally parallel to an extraction axis of the prosthesis, wherein one of said lateral legs includes an inner surface including an extraction coupler mechanically communicated to said oscillator.

4. An extraction system for a prosthesis installed and bonded into a portion of bone, the prosthesis including an exposed portion, comprising:
   an oscillation engine including a controller coupled to a vibratory machine generating an original series of pulses having a generation pattern, said generation pattern defining a first duty cycle of said original series of pulses; and
   a pulse transfer assembly having a proximal end coupled to said oscillation engine and a distal end, spaced from said proximal end, coupled to the prosthesis with said pulse transfer assembly including a connector system at said proximal end, said connector system configured to secure the exposed portion of the prosthesis producing a secured prosthesis with said pulse transfer assembly communicating an extraction series of pulses, responsive to said original series of pulses, to said secured prosthesis producing an applied series of ultrasonic pulses responsive to said extraction series of pulses;
   wherein said applied series of ultrasonic pulses are configured to impart a vibratory motion to said secured prosthesis enabling an extraction of said secured prosthesis from the portion of bone
   wherein said engine is operable in two distinctive selectable modes including a unidirectional mode providing only extractive forces and a bidirectional mode providing both extractive and insertional forces.

5. The extraction system of claim 4 wherein said pulse transfer assembly receives said original series of pulses from said oscillation engine and produces, responsive to said original series of pulses, an extraction series of pulses having an extraction pattern, said extraction pattern defining a second duty cycle of said extraction series of pulses including a second pulse amplitude, a second pulse direction, a second pulse duration, and a second pulse time window with said pulse transfer assembly communicating said extraction series of pulses to said secured prosthesis producing said applied series of ultrasonic pulses responsive to said extraction series of pulses.

6. The extraction system of claim 5 wherein said pulse transfer assembly includes a body and an elongate vibration assembly having a proximal end and a distal end opposite of said proximal end, said proximal disposed within said body and coupled to said oscillation engine with said distal end extending outside said body and including said connector system;
   said elongate vibration assembly configured to move relative to said body and having one or more degrees of freedom.

7. The extraction system of claim 4 wherein said pulse transfer assembly includes a body and an elongate vibration assembly having a proximal end and a distal end opposite of said proximal end, said proximal disposed within said body and coupled to said oscillation engine with said distal end extending outside said body and including said connector system;
   said elongate vibration assembly configured to move relative to said body and having one or more degrees of freedom.

8. An apparatus for extracting a bonded implant from a live bone of a patient, the prosthesis having an exposed portion, wherein non-vibratory revision forces for removing the bonded prosthesis from the live bone are in a first range, comprising:
   means for vibrating the bonded implant to produce a vibrating bonded implant having a predetermined vibration pattern including an oscillation; and
   means for extracting the vibrating bonded implant from the live bone using vibratory extraction forces in a second range, said second range including a set of values less than a lowest value of the first range;
   wherein said means for vibrating is operable in two distinctive selectable modes including a unidirectional mode providing only extractive forces and a bidirectional mode providing both extractive and insertional forces.

* * * * *